US012318626B2

(12) United States Patent
Lohr et al.

(10) Patent No.: US 12,318,626 B2
(45) Date of Patent: *Jun. 3, 2025

(54) FAR RED AND NEAR INFRARED LIGHT-MEDIATED CONDITIONING OF TISSUES AND/OR BLOOD TO PREVENT REPERFUSION INJURY IN ENDOVASCULAR THERAPIES

(71) Applicant: The Medical College of Wisconsin, Inc., Milwaukee, WI (US)

(72) Inventors: Nicole Lohr, New Berlin, WI (US); Michael Salinger, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/665,513

(22) Filed: May 15, 2024

(65) Prior Publication Data

US 2024/0299766 A1 Sep. 12, 2024

Related U.S. Application Data

(63) Continuation of application No. 17/701,099, filed on Mar. 22, 2022, now Pat. No. 11,998,757.

(60) Provisional application No. 63/164,751, filed on Mar. 23, 2021.

(51) Int. Cl.
*A61B 18/24* (2006.01)
*A61N 5/06* (2006.01)
*A61B 17/00* (2006.01)
*A61B 18/00* (2006.01)
*A61B 90/00* (2016.01)

(52) U.S. Cl.
CPC ............ *A61N 5/0601* (2013.01); *A61B 18/24* (2013.01); *A61N 5/0613* (2013.01); *A61B 2017/0019* (2013.01); *A61B 2018/00351* (2013.01); *A61B 2018/00577* (2013.01); *A61B 2090/049* (2016.02); *A61N 2005/0602* (2013.01); *A61N 2005/063* (2013.01); *A61N 2005/0651* (2013.01); *A61N 2005/0663* (2013.01)

(58) Field of Classification Search
CPC .............................. A61N 5/0601; A61B 18/24
USPC ........................................................ 606/15
See application file for complete search history.

(56) References Cited

U.S. PATENT DOCUMENTS

| 8,097,028 | B2 | 1/2012 | Chen et al. |
| 8,495,196 | B2 | 7/2013 | Harrang et al. |
| 10,137,158 | B2 | 11/2018 | Cohen et al. |
| 2010/0049180 | A1 | 2/2010 | Wells et al. |

*Primary Examiner* — Nadia A Mahmood
(74) *Attorney, Agent, or Firm* — Quarles & Brady LLP

(57) ABSTRACT

Reperfusion injury is limited during endovascular therapies (e.g., revascularization and/or reperfusion of end organ tissues) by conditioning the tissues against reperfusion injury using an optical fiber catheter to deliver far red and near infrared (R/NIR) light to the tissues. The light may be multiple wavelength or single wavelength light, and may have one or more wavelengths selected from the range of 510 to 830 nm. The R/NIR light may be delivered concurrently with the endovascular therapy, or in other instances may be delivered before or after a particular therapy.

15 Claims, 2 Drawing Sheets

FAR RED AND NEAR INFRARED LIGHT-MEDIATED CONDITIONING OF TISSUES AND/OR BLOOD TO PREVENT REPERFUSION INJURY IN ENDOVASCULAR THERAPIES

STATEMENT REGARDING FEDERALLY SPONSORED RESEARCH

This invention was made with government support under HL139557 awarded by the National Institutes of Health and under I01BX004675 and 1IK2BX002426 awarded by the United States Department of Veterans Affairs. The government has certain rights in the invention.

BACKGROUND

Heart disease remains a prevalent cause of death worldwide. In certain coronary heart diseases, patients may develop ST-elevation myocardial infarction ("STEMI"). Patients with STEMI are at a greater risk for developing life-threatening arrhythmias.

Myocardial reperfusion and other endovascular therapies can be used to treat STEMI. The process of restoring coronary blood flow can, however, result in so-called reperfusion injury to the underlying myocardial tissues.

Currently, there are no fully agreed upon effective clinical therapies for conditioning myocardial tissues to prevent or otherwise reduce reperfusion injury from occurring. Thus, there remains a need for cardioprotective therapies that condition myocardial tissues to prevent or otherwise reduce reperfusion injuries.

SUMMARY OF THE DISCLOSURE

The present disclosure addresses the aforementioned drawbacks by providing a method for conditioning tissues to reduce reperfusion injury. The method includes providing an optical fiber catheter to a region in a subject containing tissues. The tissues in the region are then conditioned to reduce reperfusion injury by operating a light source coupled to a proximal end of the optical fiber catheter to generate light having at least one wavelength selected from a range of 510 nm to 830 nm. The light is communicated from the proximal end of the optical fiber catheter to its distal tip where the light is emitted from the optical fiber catheter and caused to impinge upon the tissues in the region. An endovascular therapy is administered to the tissues in the region, where the tissues in the region are conditioned by the light emitted from the optical fiber such that reperfusion injury of the tissues resulting from the endovascular therapy is significantly reduced.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
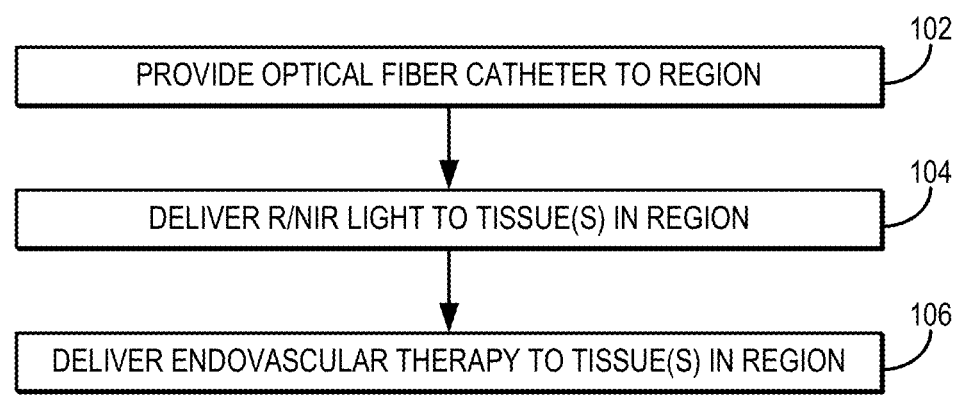
FIG. 1 is a flowchart setting forth the steps of an example method for conditioning tissues to prevent reperfusion injury in endovascular therapies using far red and near infrared ("R/NIR") light.

Described here are systems and methods for limiting reperfusion injury during endovascular therapies, such as revascularization and/or reperfusion of end organ tissues (e.g., heart, brain, kidney, extremities). In general, an optical fiber catheter or transdermal light delivery system is used to deliver light to tissues for treatment. As a non-limiting example, the optical fiber catheter and/or transdermal light delivery system can deliver multiple wavelength or single wavelength light in order to provide conditioning of an end organ tissue before, during, or after endovascular therapy.

It is an advantage of the systems and methods described in the present disclosure that by delivering transient temporary application of light at wavelengths in the far red and near infrared ("R/NIR") spectrum (e.g., 670 nm±160 nm) at the time of endovascular therapy (e.g., clinical revascularization and/or reperfusion) of end organ tissue, reperfusion injury may be limited. Additionally or alternatively, nitric oxide ("NO") generation can be achieved and/or tissue salvage can be promoted via NO-dependent pathways, either as a standalone therapy of as an adjunct to otherwise available pharmacologic and/or oxygen-mediated therapies. For example, an optimized application of R/NIR to light endothelial tissues can result in secretion of a stable NO precursor from the endothelium, which can then be reduced to NO. Thus, it is an aspect of the present disclosure that R/NIR light can be delivered directly to end organ tissues or blood to provide protection against reperfusion injury, such as by conditioning the tissues against reperfusion injury, without the need for additional measures such as the administration of exogenous sodium nitrite or other exogenous pharmacological agents into the end organ tissue or blood.

As a non-limiting example, the systems and methods described in the present disclosure can be used during transcatheter reperfusion of acute myocardial infarction ("MI"). For instance, at the time of transcatheter reperfusion and/or percutaneous coronary intervention ("PCI") for acute ST-elevation myocardial infarction ("STEMI") and/or acute coronary ischemia ("ACS"), the reperfusion injury can be limited while improving reperfusion and myocardial salvage. By delivering light in the far red and/or near infrared ("NIR") spectrum to cardiac tissue in an intracoronary approach, reperfusion injury during stenting for acute STEMI can be prevented or otherwise reduced.

Additionally or alternatively, the systems and methods described in the present disclosure can be used during transcatheter reperfusion of ischemic stroke and/or traumatic brain injury. In these instances, cerebral injury can be limited while improving brain salvage.

In still other examples, the systems and methods described in the present disclosure can be used during transcatheter reperfusion of the kidneys. In these renal reperfusion applications, renal injury can be limited during percutaneous renal artery interventions.

As still another example, the systems and methods described in the present disclosure can be used during transcatheter revascularization of ischemic limbs. For instance, in limb salvage and/or wound healing applications, reperfusion injury can be limited while otherwise improving clinical response to peripheral intra-arterial interventions.

As one non-limiting example, the systems and methods described in the present disclosure can be used with excimer laser systems to provide protective conditioning of tissues before, during, and/or after plaque ablation procedures. As another example, the systems and methods described in the present disclosure can be used with a transcatheter supersaturated oxygen ($SSO_2$) delivery system to limit infarct size and improve myocardial salvage.

Referring now to FIG. 1, a flowchart is illustrated as setting forth the steps of an example method for conditioning a tissue to prevent or otherwise reduce reperfusion injury prior to or during an endovascular or other suitable vascular therapy.

The method includes positioning or otherwise providing an optical fiber catheter and/or transdermal light delivery system to a region within a patient, as indicated at step 102. As one example, the region can include cardiac tissue, such as myocardial tissue and/or endothelial tissue. As another example, the region can include brain tissue. As still another example, the region can include renal tissue. As yet another example, the tissue can include vascular tissue, such as vascular tissue in the patient's limbs or other portions of the patient's extremities. In a non-limiting example, the vascular tissue may include endothelial tissue. In still other example, the region can include the skin surface of the patient, such that light is delivered transdermally to tissues such as dermal vasculature.

Providing the optical fiber catheter can include providing the optical fiber catheter to the region through the patient's vasculature, such as in an intracoronary application, an intraarterial application, an intravenous application, or the like. Additionally or alternatively, providing the transdermal light delivery system can include arranging the transdermal light source or coupled light guide on the skin surface of the patient.

In general, the optical fiber catheter includes one or more optical fibers that are coupled at their proximal end to a light source, such as a laser, light emitting diode ("LED"), or so on. Light energy is generated by the light source and delivered along the length of the optical fiber catheter to its distal end. At the distal end, light exits the optical fiber catheter where it impinges upon tissues in the region to which the optical fiber catheter has been provided or otherwise positioned.

Thus, after the optical fiber catheter and/or transdermal light delivery system has been provided or otherwise positioned in, or adjacent, the region, the optical fiber catheter and/or transdermal light delivery system is operated to deliver light energy to tissues in the region, as indicated at step 104. The optical fiber catheter and/or transdermal light delivery system can deliver broadband light (i.e., light of multiple wavelengths) or laser light (i.e., light with a single wavelength). As described above, the optical fiber catheter and/or transdermal light delivery system is preferably operated to generate and deliver R/NIR light to the region.

The optical fiber catheter and/or transdermal light delivery system can be operated to generate and deliver light with a wavelength of 670 nm±160 nm. As noted above, in some embodiments the light is a laser light. In these instances, the light may be generated at a single wavelength, such as 670 nm or another wavelength in the range of 510-830 nm. In other embodiments, the light contains more than one wavelength. In these instances, the light may be generated to span a range of wavelengths (i.e., the light may have a bandwidth that spans a subrange of wavelengths), such as a subrange of wavelengths within 510-830 nm. For example, the light may be generated with wavelengths within a subrange having a bandwidth of 1 nm, 2 nm, 3 nm, 4 nm, 5 nm, 10 nm, 15 nm, 20 nm, 25 nm, 30 nm, 50 nm, 100 nm, or the like.

The optical fiber catheter and/or transdermal light delivery system can be operated to generate light with an output fluence in a range of 25-170 $mW/cm^2$. For example, the output fluence of the generated light may range, in certain embodiments, from about 25 $mW/cm^2$ to about 100 $mW/cm^2$, from about 60 $mW/cm^2$ to about 170 $mW/cm^2$, or subranges therewithin. As a non-limiting example, the output fluence may, in certain embodiments, be selected as 25 $mW/cm^2$, 50 $mW/cm^2$, or the like.

The light can be delivered in a continuous or pulsed mode over a duration of time. In a pulsed mode, the light can be generated and delivered in pulses with a pulse rate in the range of 25-80 Hz with a pulse width in a range of 125-200 ns. The duration of time during which the light is delivered can be on the order of minutes (e.g., 1 minute, 2 minutes, 3 minutes, 5 minutes, etc.). As a non-limiting example, the light may be delivered for a duration of time between 5 and 15 minutes, such as for 5 minutes, for 10 minutes, for 15 minutes, and the like. In other embodiments, the light may be delivered for a duration of time greater than 15 minutes.

In some embodiments, light may be generated with parameters that are optimized for stimulating endothelial tissue to secrete a stable NO precursor, which can then be reduced to NO. As one example, light may be generated with a wavelength of 670 nm for 5-15 minutes with an intensity between 25 $mW/cm^2$ and 100 $mW/cm^2$. For example, light may be generated at a wavelength of 670 nm for 5-10 minutes with an intensity of 50 $mW/cm^2$.

In some instances, the optical fiber catheter and/or transdermal light delivery system can be controlled during its operation to adjust the wavelength of light being generated and delivered during a procedure. For instance, the optical fiber catheter can be controlled to vary the wavelength of light within a range of 510 nm to 830 nm.

By controlling the generation of light in the R/NIR spectrum and delivering it to tissues, and/or blood, in the region, NO production and/or release can be mediated to provide optimal vascular vasodilation in the tissues in the region. As a result, the tissues can be conditioned to prevent or otherwise reduce reperfusion injury.

Concurrent with the delivery of the R/NIR light, endovascular therapy is provided to the tissues in the region, as indicated at step 106. For instance, the R/NIR light can be delivered contemporaneous with the endovascular therapy. As another example, the R/NIR light can be delivered interleaved with the endovascular therapy, such as interleaved with a delivery of periods of ablation therapy. While in some applications, conditioning the tissues in the region with R/NIR light can be performed concurrently with endovascular therapy being administered to the tissues, in some other applications, conditioning the tissues in the region with R/NIR light can be performed prior to the endovascular therapy. In still other instances, the R/NIR light can be delivered after the endovascular therapy. Alternatively, the R/NIR light can be delivered in any combination of before, during, and/or after endovascular therapy.

In addition to delivering light using an optical fiber catheter that is positioned within a subject's vasculature or other organ, it is an advantage that the methods described in the present disclosure can also be implemented in transdermal applications of light. For instance, light can be generated by a light source and delivered transdermally (e.g., to the surface of the subject's skin). As a non-limiting example, it is a discovery of the present disclosure that light generated with a wavelength of 670 nm with a fluence of about 22.5 J/cm$^2$ has sufficient energy retention at a depth of 15-20 mm, which is deep enough for interaction with dermal vasculature.

Figure 2:
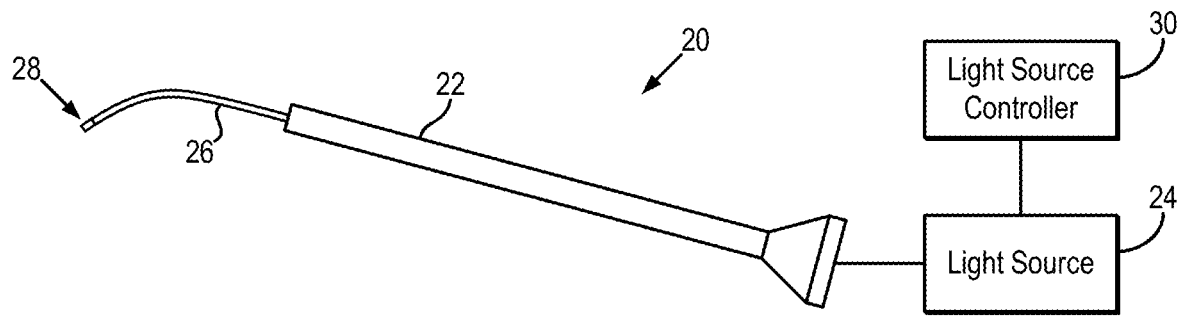
FIG. 2 shows an example optical fiber catheter system that can implement the methods described in the present disclosure.

Referring now to FIG. 2, an example optical fiber catheter system 20 that can implement the methods described in the present disclosure is shown. The optical fiber catheter system 20 generally includes a catheter 22 that is coupled at its proximal end to a light source 24. The light source may be a broadband (i.e., multiple wavelength) light source, a laser (i.e., single wavelength) light source, a light emitting diode ("LED"), or the like. As described above, the light source is preferably configured to generate light within the R/NIR spectrum, such as between 510-830 nm. The light generated by the light source 24 is delivered via one or more optical fibers 26 in the catheter 22 to the distal tip 28 of the catheter 22, where the light exits the catheter and impinges upon tissues in the region to which the catheter 22 has been positioned or otherwise provided.

The light source 24 is operated under control of a light source controller 30. The light source controller 30 can include electronic components for operating the light source 24 to vary and otherwise control the generation of the light being generated by the light source 24. For instance, the light source controller 30 can control the light source 24 to vary the wavelength of light generated, the output fluence of light generated, and the timing and duration of light generated (e.g., continuous light, pulsed light). In some embodiments, the light source controller 30 can include a computing device that can execute at least a portion of the control of the light source 24. The computing device can be any suitable computing device or combination of devices, such as a desktop computer, a laptop computer, a smartphone, a tablet computer, a wearable computer, a server computer, a virtual machine being executed by a physical computing device, and so on.

In some configurations, the optical fiber catheter system 20 can include both therapeutic and diagnostic capabilities. For example, in addition to the light source 24 providing therapeutic delivery of light as described above, the optical fiber catheter system 20 can also be configured to provide diagnostic imaging. As a non-limiting example, the optical fiber catheter system 20 can be configured to also provide optical coherence tomography ("OCT") of the subject tissues. In this way, the therapy provided by delivering light via the light source 24 can be monitored (e.g., the therapeutic effect can be imaged and/or measured), the optical catheter 22 can be guided under imaging, and the like.

Figure 3:
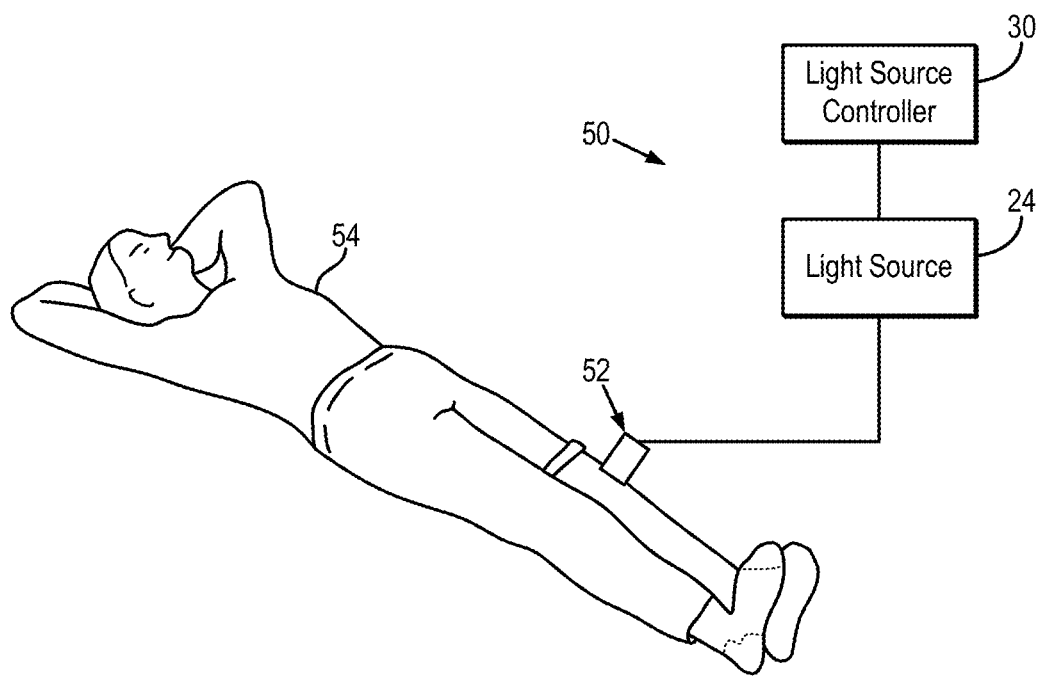
FIG. 3 shows an example transdermal light delivery system that can implement the methods described in the present disclosure.
Figure 4:
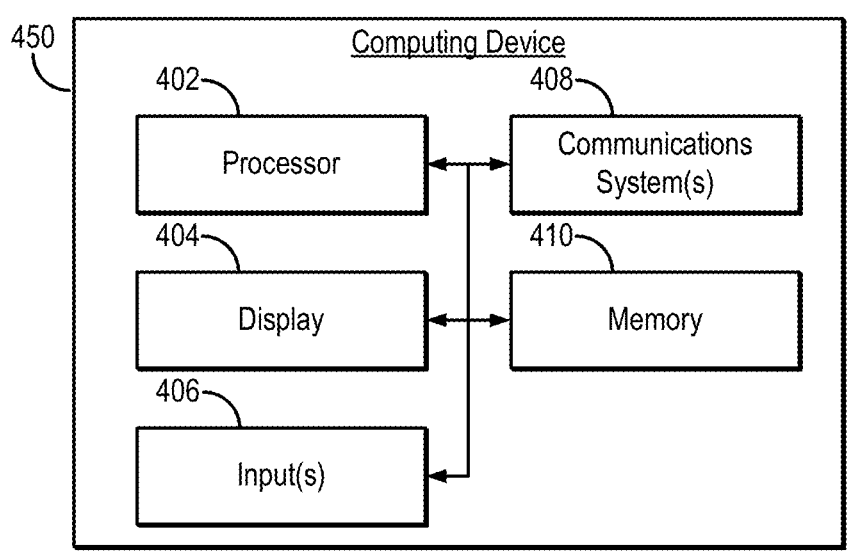
FIG. 4 is a block diagram of an example computing device that can be used to control a light source to generate R/NIR light in accordance with some embodiments described in the present disclosure.

Additionally or alternatively, a transdermal light delivery system 50 can be implemented, as illustrated in FIG. 3. The transdermal light delivery system 50 generally includes a light guide 52 that is coupled at its proximal end to a light source 24. The light source may be a broadband (i.e., multiple wavelength) light source, a laser (i.e., single wavelength) light source, an LED, or the like. As described above, the light source is preferably configured to generate light within the R/NIR spectrum, such as between 510-830 nm. The light generated by the light source 24 is delivered via the light guide 52 to impinge upon the skin of a subject 54. For instance, the light guide 52 can be arranged on the skin surface of the subject 54 such that the light generated by the light source 24 exits the light guide 52 and impinges upon the skin surface.

The light guide 52 can take different forms. As one example, the light guide 52 can include an objective or other optical coupling device that is optically coupled to the light source 24 via one or more optical fibers and configured to transmit light received by the light source 24 outward from the light guide 52 to impinge upon the skin surface of the subject 24. As another example, the light guide 52 can be an objective or other optical coupling device that is directly coupled to the light source 24, such that the light source 24 and light guide 52 can be moved in unison over the skin surface of the subject 52. For instance, the light source 24 and light guide 52 may be housed within a common housing. In still other embodiments, the transdermal light delivery system 50 may not include a light guide 52. In these configurations, the light source 24 can be positioned directly on the skin surface of the subject 54.

The light source 24 is operated under control of a light source controller 30. The light source controller 30 can include electronic components for operating the light source 24 to vary and otherwise control the generation of the light being generated by the light source 24. For instance, the light source controller 30 can control the light source 24 to vary the wavelength of light generated, the output fluence of light generated, and the timing and duration of light generated (e.g., continuous light, pulsed light). In some embodiments, the light source controller 30 can include a computing device that can execute at least a portion of the control of the light source 24. The computing device can be any suitable computing device or combination of devices, such as a desktop computer, a laptop computer, a smartphone, a tablet computer, a wearable computer, a server computer, a virtual machine being executed by a physical computing device, and so on.

As shown in FIG. 3, in some embodiments, an example computing device 450 can include a processor 402, a display 404, one or more inputs 406, one or more communication systems 408, and/or memory 410. In some embodiments, processor 402 can be any suitable hardware processor or combination of processors, such as a central processing unit ("CPU"), a graphics processing unit ("GPU"), and so on. In some embodiments, display 404 can include any suitable display devices, such as a computer monitor, a touchscreen, a television, and so on. In some embodiments, inputs 406 can include any suitable input devices and/or sensors that can be used to receive user input, such as a keyboard, a mouse, a touchscreen, a microphone, and so on.

In some embodiments, communications systems 408 can include any suitable hardware, firmware, and/or software for communicating information over a communication network and/or any other suitable communication networks. For example, communications systems 408 can include one or more transceivers, one or more communication chips and/or chip sets, and so on. In a more particular example, communications systems 408 can include hardware, firmware and/or software that can be used to establish a Wi-Fi connection, a Bluetooth connection, a cellular connection, an Ethernet connection, and so on.

In some embodiments, memory 410 can include any suitable storage device or devices that can be used to store instructions, values, data, or the like, that can be used, for example, by processor 402 to present content using display 404, to communicate with a server via communications system(s) 408, and so on. Memory 410 can include any suitable volatile memory, non-volatile memory, storage, or any suitable combination thereof. For example, memory 410 can include RAM, ROM, EEPROM, one or more flash drives, one or more hard disks, one or more solid state drives, one or more optical drives, and so on. In some embodiments, memory 410 can have encoded thereon, or otherwise stored therein, a computer program for controlling operation of computing device 450. In such embodiments, processor 402 can execute at least a portion of a computer program to control the operation of the light source 24.

The present disclosure has described one or more preferred embodiments, and it should be appreciated that many equivalents, alternatives, variations, and modifications, aside from those expressly stated, are possible and within the scope of the invention.

The invention claimed is:

1. A method for conditioning tissues in a subject to reduce reperfusion injury, the method comprising:
illuminating a region in a subject containing tissues with light from a light source having at least one wavelength selected from a range of 510 nanometers (nm) to 670 nm, wherein the tissues in the region are conditioned by the light emitted from the light source such that reperfusion injury of the tissues resulting from an endovascular therapy is significantly reduced.

2. The method of claim 1, wherein the light source is coupled to a proximal end of an optical fiber catheter.

3. The method of claim 1, wherein the light source is a laser light source and the light is laser light having a single wavelength selected from the range of 510 nm to 670 nm.

4. The method of claim 3, wherein the laser light has a single wavelength of 670 nm.

5. The method of claim 1, further comprising administering an endovascular therapy to the tissues in the region.

6. The method of claim 5, wherein the light is generated and delivered to the tissues in the region concurrently with the endovascular therapy.

7. The method of claim 1, wherein the tissues in the region comprise blood.

8. The method of claim 4, wherein the tissues in the region include myocardial tissues.

9. The method of claim 1, wherein the light is generated by the light source and delivered in a continuous delivery.

10. The method of claim 1, wherein the light is generated by the light source and delivered in a pulsed delivery, such that the light is generated and delivered in a series of pulses at a pulse rate selected from a range of 25 Hertz (Hz) to 80 Hz.

11. The method of claim 10, wherein each pulse in the series of pulses has a pulse width selected from a range of 125 nanoseconds (ns) to 200 ns.

12. The method of claim 1, wherein the light is generated by the light source with an intensity in a range of 25 $mW/cm^2$ and 170 $mW/cm^2$.

13. The method of claim 12, wherein the light is generated by the light source with an intensity of 50 $mW/cm^2$ for a duration of time in a range of 5 minutes to 10 minutes.

14. The method of claim 1, wherein the light source is a transdermal light source, such that illuminating the region in a subject containing tissues with light from the light source comprises illuminating a skin surface of the subject.

15. The method of claim 14, wherein the light source is a light emitting diode (LED) light source.

* * * * *